United States Patent [19]

Oeckl et al.

[11] Patent Number: 4,661,632
[45] Date of Patent: Apr. 28, 1987

[54] HALOGENOPROPARGYLFORMAMIDE PESTICIDES

[75] Inventors: Siegfried Oeckl, Bergisch-Gladbach; Paul Reinecke, Leverkusen; Wilhelm Brandes, Leichlingen; Karl-Heinz Kuck, Langenfeld; Wilfried Paulus; Hermann Genth, both of Krefeld, all of Fed. Rep. of Germany

[73] Assignee: Bayer Aktiengesellschaft, Leverkusen, Fed. Rep. of Germany

[21] Appl. No.: 793,600

[22] Filed: Oct. 31, 1985

Related U.S. Application Data

[63] Continuation of Ser. No. 490,898, May 2, 1983.

[30] Foreign Application Priority Data

May 18, 1982 [DE] Fed. Rep. of Germany ....... 3218611
Oct. 2, 1982 [DE] Fed. Rep. of Germany ....... 3236522

[51] Int. Cl.$^4$ .......................................... C07C 103/34
[52] U.S. Cl. .................................. 564/217; 564/215; 564/218; 564/219
[58] Field of Search ............... 564/215, 217, 218, 219; 424/320; 514/650, 659, 666

[56] References Cited

FOREIGN PATENT DOCUMENTS 0010673 5/1980 European Pat. Off. ............ 564/218
2251205 5/1974 Fed. Rep. of Germany ...... 564/217
2919196 11/1980 Fed. Rep. of Germany ...... 564/218

*Primary Examiner*—Charles F. Warren
*Assistant Examiner*—John A. Sopp
*Attorney, Agent, or Firm*—Sprung Horn Kramer & Woods

[57] ABSTRACT

Halogenopropargylformamides of the formula

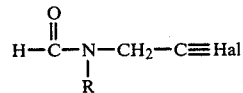

in which
R is hydrogen, alkyl, halogenoalkyl, cycloalkyl, halogenoalkyl, cycloalkyl, alkenyl, alkinyl, halogenoalkinyl, optionally substituted aralkyl and optionally substituted aryl, and
Hal is halogen.

which possess fungicidal and bactericidal properties.

6 Claims, No Drawings

HALOGENOPROPARGYLFORMAMIDE PESTICIDES

This is a continuation of application Ser. No. 490,898, filed May 2, 1983.

The present invention relates to new halogenopropargylformamides, a process for their preparation, and their use as pest-combating agents.

Heavy metal salts of ethylene-1,2-bis-(dithiocarbamic acid), in particular zinc ethylene-1,2-bis-(dithiocarbamate), have long been used in agriculture and horticulture for combating phytopathogenic fungi (see R. Wegler, "Chemie der Pflanzenschutz- und Schädlingsbekämpfungsmittel" [Chemistry of Plant Protection Agents and Pest-combating Agents], Volume 2, page 65, Springer-Verlag Berlin/Heidelberg/New York [1970]).

Furthermore, it has long been known that compounds containing N-trihalogenomethylthio groups are used as fungicides in agriculture and horticulture. Thus, for example, N-(trichloromethylthio)-tetrahydrophthalimide is used in practice in fruit cultivation and viticulture for combating fungal diseases (see German Patent Specification No. 887,506 and Angew. Chem. 76, 807 [1964]).

Furthermore, inorganic copper compounds which have a broad fungicidal spectrum of action are known (see K. H. Büchel, "Pflanzenschutz und Schädlingsbekämpfung" [Plant Protection and Pest-combating], pages 121 and 122, Georg Thieme Verlag Stuttgart). In addition, iodopropargyl compounds, such as N-butyl iodopropargyl carbamate, have been disclosed as paint fungicides (see DE-OS [German Published Specification] No. 3,116,653).

New halogenopropargylformamides of the formula (I)

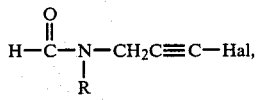

in which
R represents hydrogen, alkyl, halogenoalkyl, cycloalkyl, alkenyl, alkinyl, halogenoalkinyl, optionally substituted aralkyl and optionally substituted aryl and
Hal represents halogen,
have been found.

The new halogenopropargylformamides of the formula (I),

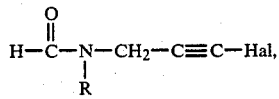

in which
R represents hydrogen, alkyl, halogenoalkyl, cycloalkyl, alkenyl, alkinyl, halogenoalkinyl, optionally substituted aralkyl and optionally substituted aryl and
Hal represents halogen,
are obtained when propargylformamides of the formula (II)

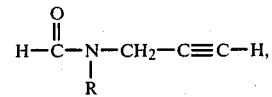

in which R has the meaning given above,
are reacted with halogenating agents in the presence of basic substances in a diluent at temperatures between $-30°$ C. and $+50°$ C.

The new halogenopropargylformamides of the formula (I) have powerful fungicidal and bactericidal properties. Surprisingly, they exhibit a superior action compared with the previously known compounds.

Because their superior biological properties may be used in a number of possible ways, the compounds according to the invention represent a valuable enrichment of the art.

Among the halogenopropargylformamides according to the invention, of the formula (I), those compounds are preferred in which
R represents hydrogen, alkyl having 1 to 20 carbon atoms, halogenoalkyl having 1 to 5 halogen atoms and 1 to 8 carbon atoms, cycloalkyl having 5 to 10 carbon atoms, alkenyl having 2 to 6 carbon atoms, alkinyl having 2 to 6 carbon atoms, halogenoalkinyl having 1 to 3 halogen atoms and 2 to 6 carbon atoms, or aralkyl which has 1 to 6 carbon atoms in the alkyl radical and 6 to 10 carbon atoms in the aryl radical and is optionally monosubstituted to pentasubstituted in the aryl part by identical or different substituents from amongst alkyl having 1 to 6 carbon atoms and halogen, or represents aryl which is optionally monosubstituted to pentasubstituted by identical or different substituents from amongst alkyl having 1 to 6 carbon atoms, halogen, nitro, alkoxy having 1 to 6 carbon atoms, halogenoalkyl having 1 to 5 halogen atoms and 1 to 6 carbon atoms and halogenoalkylthio having 1 to 5 halogen atoms and 1 to 6 carbon atoms, and
Hal represents fluorine, chlorine, iodine or bromine.

Among the halogenopropargylformamides according to the invention, of the formula (I), those compounds are particularly preferred in which
R represents hydrogen, alkyl having 1 to 18 carbon atoms, such as methyl, ethyl, n- and isopropyl, n-, sec.-, tert.- and iso-butyl, pentyl, hexyl, 2-ethylhexyl, octyl, undecyl, dodecyl and stearyl, halogenoalkyl having 1 to 5 halogen atoms and 1 to 4 carbon atoms, cycloalkyl having 5 to 7 carbon atoms, such as cyclopentyl, cyclohexyl and cycloheptyl, alkenyl having 2 to 4 carbon atoms, such as vinyl, propenyl or butenyl, alkinyl having 3 or 4 carbon atoms, such as propinyl or butinyl, halogenoalkinyl having 1 or 2 halogen atoms and 3 to 5 carbon atoms, or optionally substituted aralkyl having 1 or 2 carbon atoms in the alkyl part and 6 carbon atoms in the aryl part, such as benzyl or phenethyl, and the aryl radical can be preferably monosubstituted to pentasubstituted by identical or different substituents from amongst alkyl having 1 to 4 carbon atoms, such as methyl, ethyl, n- or iso-propyl, n-, sec.-, tert.- or iso-butyl, and halogen, such as fluorine, chlorine or bromine, and furthermore represents phenyl which is optionally monosubstituted to pentasubstituted by identical or different substituents. The following may be mentioned as substituents: halogen, such as fluorine, chlorine, bromine and iodine, nitro, alkyl having 1 to 4 carbon atoms, alkoxy having 1 to 4 carbon atoms, halogenoalkyl having 1 to 5 halogen atoms and 1 to 4 carbon atoms, such as trifluoromethyl, trichloromethyl and trichloroethyl, and halogenoalkylthio having 1 to 5 halogen atoms and 1 to 4 carbon atoms, and Hal represents iodine or bromine.

Very particularly preferred compounds of the formula (I) are those in which

R represents hydrogen, alkyl having 1 to 18 carbon atoms, or phenethyl and benzyl which is optionally monosubstituted to trisubstituted by identical or different substituents from amongst methyl, ethyl and chlorine, or represents phenyl which is optionally monosubstituted to trisubstituted by identical or different substituents from amongst nitro, methyl, ethyl, n- and iso-propyl, trifluoromethyl, methoxy, ethoxy, n-propoxy, iso-propoxy, trifluoromethylthio and trichloromethylthio, and Hal represents iodine or bromine.

In addition to the preparation examples, the following halogenopropargylformamides may be mentioned individually as examples:

bromopropargylformamide, iodopropargylmethylformamide, iodopropargyloctylformamide, iodopropargyldodecylformamide, iodopropargylformanilide, 2-chloro-iodopropargylformanilide, 3-chloro-iodopropargylformanilide, 4-chloroiodopropargylformanilide, 2,3-dichloro-iodopropargylformanilide, 2,4-dichloro-iodopropargylformanilide, 3,4-dichloro-iodopropargylformanilide, 3,5-dichloro-iodopropargylformanilide, 2,4,6-trichloro-iodopropargylformanilide, 2-methyl-iodopropargylformanilide, 3-methyliodopropargylformanilide, 4-methyl-iodopropargylformanilide, 2,3-dimethyl-iodopropargylformanilide, 2,6-dimethyl-iodopropargylformanilide, 2-methyl-6-ethyliodopropargylformanilide, 3-trifluoromethyl-iodopropargylformanilide, 3,5-bis-trifluoromethyl-iodopropargylformanilide, 3-nitro-iodopropargylformanilide, bromopropargylformanilide and 3-chloro-bromopropargylformanilide.

When, for example propargylformamide and iodine are used as starting materials, the course of the reaction in the process according to the invention can be represented by the following equation:

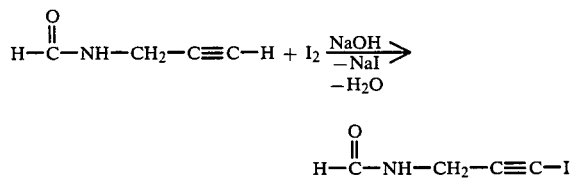

Formula (II) gives a definition of the propargylformamides to be employed as starting materials in carrying out the process. The majority of the compounds are known or can be prepared by known processes, for example by reacting an appropriate formamide with, for example, potassium tert.-butylate to give the potassium salt of the formamide, and this is reacted with a propargyl halide. However, it is also possible to react a primary amine with a propargyl halide in the presence of a base and to formylate the resulting propargylamine with formic acid or a formate (see, for example, Bull. Soc. Chim. Fr. 1967 [2], pages 588–596).

The halogenating agents, such as halogen, which are furthermore to be used as starting materials are commercial, readily available products.

Water and polar organic solvents are suitable diluents in the process. Suitable polar organic solvents are those which are inert under the reaction conditions. It is advantageous to use those organic solvents which have a certain dissolving power for the reactants. Preferably, solvents containing hydroxyl groups, such as, for example, alcohols, are used. Particularly suitable alcohols are the typical lower aliphatic alcohols, such as, for example, methanol, ethanol and isopropanol, as well as di- and polyhydroxy compounds, such as ethylene gylcol and polyethylene glycol. The reaction is particularly preferably carried out in methanol and water.

Suitable basic substances are alkali metal hydroxides and alkaline earth metal hydroxides, but alkali metal hydroxides, such as, for example, sodium hydroxide or potassium hydroxide, are preferably used.

Suitable halogenating agents are elementary halogen and hypohalites. The hypohalites are formed when halogen is added to the abovementioned alkaline solutions, but may also be prepared from halogen and alkalis before the halogenation reaction and then added to the material to be halogenated. Iodine and bromine may be mentioned in particular.

The reaction temperature can be $-30°$ to $+50°$ C., but is preferably in the range of $0°-20°$ C.

The process according to the invention can, for example, be carried out as follows:

A propargylformamide of the formula (II), in one of the diluents given, is initially introduced, and the molar amount to three times the molar amount of alkali, preferably 1.5 times the molar amount, is added. Thereafter, at least a molar amount of halogenating agent is added in portions, an excess of the halogenating agent having no disadvantages, and stirring is continued in the temperature range from 0° to 20° C. The reaction is monitored by thin-layer chromatography. After the reaction is complete, the mixture is worked up by customary methods, for example by precipitating the end product by the addition of water, or by extraction.

The active compounds according to the invention exhibit a powerful microbicidal action and can be employed in practice for combating undesired microorganisms. The active compounds are suitable for use as plant protection agents and as microbicidal agents for protecting industrial materials.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Leptosphaeria nodorum and *Fusarium nivale* in cereals, as well as against Venturia in apples and against *Xanthomonas oryzae* in rice.

Furthermore, the broad fungicidal action in the agar plate test should be mentioned. When an appropriate dose is administered, acaricidal actions are also to be observed.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example calcite, marble, pumice, sepiolite and dolomite, as well as synthetic granules or organic material such as sawdust, coconut shells, corn cobs and tobacco stalks; as emulsifying and/or foam-forming agents there are suitable: for example non-ionic and anionic emulsifiers, such as polyoxy-ethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.01% by weight, preferably 0.0001 to 0.02%, are required at the place of action. The compounds according to the invention are also suitable for the protection of industrial materials.

Within the scope of the present invention, industrial materials are products which themselves do not occur naturally but are manufactured from natural or synthetic starting materials. Within the scope of the present invention, the products to be protected are industrial materials which can be infested and/or decomposed by micro-organisms.

Industrial material which are to be protected by the substances according to the invention from microbial modification and destruction are, for example, adhesives, glues, papers, cardboards, textiles, leather, wood, coating compositions, plasters, cooling lubricants, sealing compositions and plastic articles, which can be infested or decomposed by micro-organisms. Within the scope of the materials to be protected, parts of production plants, such as, for example, cooling water circulations and cooling lubricant circulations, the operational efficiency of which can be adversely affected by micro-organisms may also be mentioned. Preferably, the active compounds according to the invention can be used for protecting adhesives, paper, cardboard, coating films, wood and the like.

Micro-organisms which can cause degradation or modification of the industrial materials are, for example, bacteria, fungi, yeasts, algae and slime organisms. Preferably, the substances according to the invention have a powerful and broad action against fungi; the fungicidal action embraces molds as well as wood-destroying and wood-discoloring fungi.

For example, micro-organisms of the following genera may be mentioned:
Alternaria, such as *Alternaria tenuis,*
Aspergillus, such as *Aspergillus niger,*
Aureobasidium, such as *Aureobasidium pullulans,*
Chaetomium, such as *Chaetomium globosum,*
Coniophora, such as *Coniophora cerebella,*
Lentinus, such as *Lentinus tigrinus,*
Penicillium, such as *Penicillium glaucum,*
Polyporus, such as *Polyporus versicolor,*

Sclerophoma, such as *Sclerophoma pityophila*, Trichoderma, such as *Trichoderma viride*.

Depending on their field of use, the substances according to the invention can be converted into the customary formulations, such as solutions, emulsions, suspensions, powders, pastes and granules. These can be prepared in a known manner, for example by mixing the active compounds with an extender which consists of a liquid solvent and/or solid carriers, optionally with the use of surface-active agents, such as emulsifiers and/or dispersing agents, and, for example in the case of the use of extenders, organic solvents can, if appropriate, be used as auxiliary solvents.

Organic solvents for the active compounds can be, for example, alcohols, such as lower alcohols, preferably ethanol or isopropanol, or benzyl alcohol, ketones, such as acetone or methyl ethyl ketone, liquid hydrocarbons, such as petroleum fractions, and chlorinated hydrocarbons, such as 1,2-dichloroethane.

The microbicidal agents according to the invention contain in general 10 to 100% by weight, preferably 50 to 80% by weight, of the halogenopropargylformamides as the active compound.

The use concentration of the substances according to the invention depends on the type and occurrence of the micro-organisms to be combated, and on the composition of the material to be protected. The optimum amount to be used can be determined by test series. In general the use concentrations are in the range from 0.001 to 5% by weight, preferably from 0.01 to 1% by weight, relative to the material to be protected.

The new active compounds according to the invention can also be present as a mixture with other known active compounds. The following active compounds may be mentioned as examples: benzimidazolyl carbamates, trihalogenomethylthio compounds, such as N-fluorodichloromethylthio-phthalimide and N,N-dimethyl-N'-phenyl-N'-(fluorodichloromethylthio)-sulphamides, compounds which split off formaldehyde, such as hemiformals, phenol derivatives, such as p-chloro-m-cresol, 2-phenyl-phenol and (2,2'-dihydroxy-5,5'-dichloro)-diphenylmethane, dithiocarbamates, thiazolylbenzimidazole, isothiazolone and benzisothiazolone derivatives, tetrachloroisophthalic acid dinitrile, mercaptobenzothiazole and mercaptopyridine.

PREPARATION EXAMPLES

Example 1

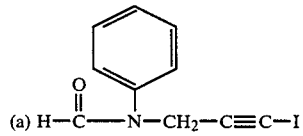

32 g (0.2 mol) of propargylformanilide are dissolved in 600 ml of methanol, and a solution of 10 g (0.25 mol) of sodium hydroxide in 30 ml of water is added at 0°–5° C. 51 g (0.2 mol) of iodine are then metered in, in several portions, in the course of one hour at 0° C., and the mixture is stirred for a further 4 hours at 0° C. A thin-layer chromatogram now shows that the starting material is completely converted. To work up the mixture, it is stirred into a mixture of 2 liters of ice water and 10 ml of 40% strength sodium bisulphite solution (to decolorize residual amounts of iodine), crystallization taking place after some time. The crystals are filtered off under suction, washed with water and dried. The yield is 44 g (77% of theory) of beige-colored crystals of N-iodopropargyl-N-formylanilide, which, after recrystallization from methanol, melts at 78° C.

The starting material used in Example 1 is prepared in the following manner:

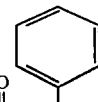
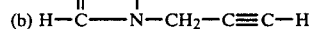

97 g (0.8 mol) of formanilide are dissolved in 400 ml of tetrahydrofuran, and 90 g (0.8 mol) of potassium tertiary-butylate in 400 ml of tetrahydrofuran are added. After the exothermic reaction (salt formation) has ceased, the mixture is evaporated to dryness in a rotary evaporator. The residue is introduced, in portions, into a solution of 60 g (0.8 mol) of propargyl chloride in 500 ml of dimethylformamide at 0°–5° C., and the mixture is then slowly warmed to room temperature and stirred for a further 20 hours until, according to the thin-layer chromatogram, complete conversion has taken place. The mixture is evaporated down and extracted by shaking with methylene chloride/water, and the organic phase is separated off, evaporated down and distilled in vacuo. The fraction in the range 105°–120° C./1.5 mm Hg is propargylformanilide. The yield is 96 g (75% of theory). The product can be employed, without further purification, for iodination.

Example 2

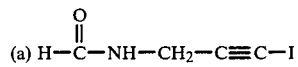

42 g (0.5 mol) of propargylformamide are dissolved in 1 liter of methanol, a solution of 25 g (0.6 mol) of sodium hydroxide in 80 ml of water is added in portions, at 0° C., and 130 g (0.5 mol) of iodine are added in portions, at the same temperature. The mixture is then stirred for a further 4 hours at 0° C. and stirred into a solution of 5 ml of 40% strength sodium bisulphite solution in 2 liters of water, the mixture is extracted by shaking with 3 times 300 ml of methylene chloride, and the organic phase is separated off, dried over sodium sulphate and evaporated down. The crude yield of 45 g is chromatographed over a silica gel column, using ethyl acetate as the mobile phase. 31 g (57% of theory) of pale crystals of iodopropargylformamide are obtained which, after recrystallization from water, melt at 86°–88° C.

The propargylformamide used in Example 2 is prepared in the following manner:

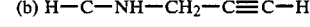

45 g (1 mol) of freshly distilled formamide in 600 ml of dimethylformamide are initially introduced, 172 g (1.25 mols) of potassium carbonate and 186 g (2.5 mols) of chloropropyne are added, and the mixture is heated. The exothermic reaction which begins at about 80°–90° C. is kept at 100° C. by slight cooling, and the mixture is then stirred for a further 15 hours at 100° C. The mixture is then evaporated down in a rotary evaporator, and the residue is fractionated by column chromatography over silica gel, using ethyl acetate as the mobile phase. 42 g (56% of theory) of a pale liquid are obtained which can be distilled at 120°–125° C./20 mbars.

The halogenopropargylformamides of the formula (I)

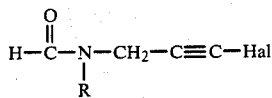

which are described below can be prepared analogously to the Preparation Example 1 or 2 described above:

| Example No. | R | Hal | Melting point [°C.] | Yield [% of theory] |
|---|---|---|---|---|
| (3) |  | I | 70–80 | 55 |
| (4) |  | I | 83–84 | 52 |
| (5) | 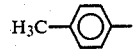 | I | 84–87 | 79 |
| (6) |  | I | 85–90 | 61 |
| (7) |  | I | 88–90 | 92 |
| (8) |  | I | 91–97 | 31 |
| (9) |  | I | 107–109 | 48 |
| (10) |  | I | 86–90 | 8 |
| (11) |  | I | 114–119 | 86 |
| (12) |  | I | 78–81 | 56 |

-continued

| Example No. | R | Hal | Melting point [°C.] | Yield [% of theory] |
|---|---|---|---|---|
| (13) | Cl-phenyl- | I | 88–89 | 32 |
| (14) | 2,3-diCl-phenyl- | I | 78–81 | 48 |
| (15) | 3,4-diCl-phenyl- | I | 79–81 | 33 |
| (16) | 3,5-diCl-phenyl- | I | 98–102 | 43 |
| (17) | 2,3-diCl-phenyl- | I | | |
| (18) | 2,4,6-triCl-phenyl- | I | 82–84 | 36 |
| (19) | 3-NO$_2$-phenyl- | I | 117–119 | 16 |
| (20) | phenyl- | Br | | 85 |
| (21) | 2-Cl-phenyl- | Br | | |

The propargylformamides of the formula (II) which are used as starting compounds were prepared analogously to Examples 1(b) and 2(b):

$$H-\overset{O}{\underset{}{C}}-\underset{R}{N}-CH_2-C\equiv C-H \quad (II)$$

| R | Melting point [°C.]; boiling point [°C./mbar], refractive index [n$_D^{20}$] | Yield [% of theory] |
|---|---|---|
| 2-CH$_3$-phenyl- | 43–45 | 69 |
| 3-CH$_3$-phenyl- | 1.5470 | 69 |

-continued $$\text{H}-\overset{\overset{\text{O}}{\|}}{\text{C}}-\underset{\underset{\text{R}}{|}}{\text{N}}-\text{C}\equiv\text{C}-\text{H} \quad (II)$$

| R | Melting point [°C.]; boiling point [°C./mbar], refractive index [$n_D^{20}$] | Yield [% of theory] |
|---|---|---|
| CH₃—⌬— | 158/12 | 58 |
| 2,6-(CH₃)₂-C₆H₃— | 52–54 | 82 |
| 2,4-(CH₃)₂-C₆H₃— | 57–59 | 32 |
| 2-CH₃-6-C₂H₅-C₆H₃— | 1.5020 | 98 |
| 3-CF₃-C₆H₄— | 1.5328 | 52 |
| 3,5-(F₃C)₂-C₆H₃— | 52–54 | 75 |
| 2-Cl-C₆H₄— | 107–8/0.8 | 63 |
| 3-Cl-C₆H₄— | 44–46 | 28 |
| 4-Cl-C₆H₄— | 51–53 | 81 |
| 2,3-Cl₂-C₆H₃— | 72–74 | 96 |
| 3,4-Cl₂-C₆H₃— | 71–73 | 77 |
| 3,5-Cl₂-C₆H₃— | 77–80 | 68 |
| 3,4-Cl₂-C₆H₃— | 69–71 | 66 |
| 2,3,4-Cl₃-C₆H₂— | 70–72 | 86 |
| 3-NO₂-C₆H₄— | 82–83 | 68 |
| 4-O₂N-C₆H₄— | 114–16 | 31 |

The known compounds indicated below are employed as comparative substances in the examples which follow:

(A) Zinc ethylenebis(dithiocarbamate):

$$\begin{array}{c}\text{CH}_2-\text{NH}-\overset{\overset{\text{S}}{\|}}{\text{C}}-\text{S}\\|\phantom{xxxxxxxxxxxxxx}\diagdown\text{Zn}\\\text{CH}_2-\text{NH}-\overset{\overset{\text{S}}{\|}}{\text{C}}-\text{S}\diagup\end{array}$$

(B) Captan-type: N-(trichloromethylthio)-4-cyclohexene-1,2-dicarboximide (C) $3 \times \text{Cu(OH)}_2 \times \text{CuCl}_2 \times \text{H}_2\text{O}$ (D) $\text{n-C}_4\text{H}_9-\text{NH}-\overset{\overset{\text{O}}{\|}}{\text{C}}-\text{O}-\text{CH}_2-\text{C}\equiv\text{C}-\text{I}$ Example A

*Leptosphaeria nodorum* test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 5, 7, 6, 9, 12, 13, 14, 15 and 16.

Example B

*Fusarium nivale* test (rye)/seed treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the rye are sown 1 cm deep in standard soil and are cultivated in a greenhouse at a temperature of about 10° C. and a relative atmospheric humidity of 95%, in seedboxes which are exposed to light for 15 hours daily.

About 3 weeks after sowing, the plants are evaluated for symptoms of snow mold.

In this test, a clearly superior activity compared with the prior art is shown, for example, by the compounds according to the following preparation examples: 5 and 9.

Example C

Venturia test (apple)/protective
Solvent:
  4.7 parts by weight of acetone
  0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 15, 13 and 17.

Example D

*Xanthomonas oryzae* test/bacteriosis/rice/systemic
Solvent: 121.25 parts by weight of acetone
Emulsifier: 3.75 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for systemic properties, standard soil in which young plants have been grown is watered with 100 ml of the preparation of active compound. 3 days after the treatment, the plants are inoculated with an aqueous suspension of *Xanthomonas oryzae* by pricking. Thereafter, the plants remain in a greenhouse at 24° to 26° C. and 70 to 80% relative atmospheric humidity for 14 days until they are evaluated.

In this test, a clearly superior activity compared with the prior art is shown, for example, by the compounds according to the following preparation examples: 1, 16, 12 and 9.

Example E

Action against fungi

The compounds according to the invention were incorporated, in stepwise concentrations between 1 and 500 mg/liter of test sample, into an agar prepared from beer-wort and peptone. After the agar had solidified, the agar samples thus prepared were contaminated with pure cultures of various test fungi.

After storage for 2 weeks at 28° C. and 60 to 70% relative atmospheric humidity, the evaluation was carried out. The minimum inhibitory concentration (MIC), that is to say the lowest concentration of the substance, present in an agar sample, at which no growth of the species used took place, was given.

In this test, a clearly superior activity compared with the prior art was shown, for example, by the compounds according to the following preparation examples: 11, 12, 13, 15, 17, 18, 5, 7, 14, 3, 4, 6 and 19.

It will be appreciated that the instant specification and examples are set forth by way of illustration and not limitation, and that various modifications and changes may be made without departing from the spirit and scope of the present invention.

We claim:

1. A halogenopropargylformamide of the formula

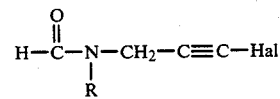

in which
  R is phenyl which is monosubstituted to trisubstituted by substituents selected from the group consisting of nitro, halogen, halogenoalkyl having 1 to 5 halogen atoms and 1 to 6 carbon atoms, and halogenoalkylthio having 1 to 5 halogen atoms and 1 to 6 carbon atoms, with the proviso that R is not phenyl monosubstituted with chloro in the position ortho to the nitrogen, and
  Hal is fluorine, chlorine, iodine or bromine.

2. A pesticidal composition comprising a pesticidally effective amount of a compound according to claim 1 in admixture with a diluent.

3. A method of combating pests which comprises applying to the pests or a pest habitat a pesticidally effective amount of a compound according to claim 1.

4. A halogenpropargylformamide according to claim 1,
in which Hal is iodine.

5. A halogenopropargylformamide according to claim 1,
in which R is phenyl which is monosubstituted to trisubstituted by chlorine.

6. A halogenopropargylformamide according to claim 5,
in which Hal is iodine.

* * * * *